(12) United States Patent
Luerkens

(10) Patent No.: US 9,160,248 B2
(45) Date of Patent: Oct. 13, 2015

(54) VOLTAGE MULTIPLIER

(71) Applicant: KONINKLIJKE PHILIPS N.V., Eindhoven (NL)

(72) Inventor: Peter Luerkens, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/400,567

(22) PCT Filed: May 31, 2013

(86) PCT No.: PCT/IB2013/054497
§ 371 (c)(1),
(2) Date: Nov. 12, 2014

(87) PCT Pub. No.: WO2013/190412
PCT Pub. Date: Dec. 27, 2013

(65) Prior Publication Data
US 2015/0139391 A1    May 21, 2015

Related U.S. Application Data

(60) Provisional application No. 61/661,858, filed on Jun. 20, 2012.

(51) Int. Cl.
*H05G 1/10* (2006.01)
*H02M 7/10* (2006.01)
*G01N 23/04* (2006.01)
*H02M 3/07* (2006.01)

(52) U.S. Cl.
CPC ............... *H02M 7/103* (2013.01); *G01N 23/04* (2013.01); *H02M 3/07* (2013.01); *H05G 1/10* (2013.01)

(58) Field of Classification Search
CPC ........ G01N 23/04; H02M 3/07; H02M 7/103; H02M 3/28; H02M 7/106; H02M 2001/007; H02M 7/08; H02M 7/217; H02M 2001/0045; H02M 2003/078; H02M 3/156; H02M 3/158; H02M 3/33569; H02M 3/337; H02M 7/10; H05G 1/10; H05G 1/34; H05G 1/20; H05G 1/02; H05G 1/32; H01J 2235/087; H01J 35/04; H01J 35/16
USPC .......................... 378/101, 106, 107, 114, 117
See application file for complete search history.

(56) References Cited

U.S. PATENT DOCUMENTS 4,646,338 A * 2/1987 Skillicorn ..................... 378/110
(Continued)

FOREIGN PATENT DOCUMENTS

| BE | 1013646 A6 | 5/2002 |
| WO | 2007017793 A1 | 2/2007 |
| WO | 2011151767 A1 | 12/2011 |

*Primary Examiner* — Irakli Kiknadze

(57) ABSTRACT

A voltage multiplier 10 comprises a series of multiplier stages 12a, 12b, 12c, 12d. Each multiplier stage, for example 12b, comprises a first input 16b, a second input 14b, a first output 16c and second output 14c. The first and second outputs of a preceding multiplier stage are interconnected with first and second inputs of a subsequent multiplier stage. Furthermore, each multiplier stages, for example 12b, comprises two series connected diode elements D5, D6 having the same current conducting direction. The two series connected diode elements D5, D6 interconnect the first input 16b and the first output 16c. The second output 14c is coupled between the two series connected diode elements D5, D6. Each multiplier stage, for example 12b, comprises a buffer capacitor C6 interconnecting the respective first input 16b and the respective first output 16c. At least some multiplier stages, for example 12b, comprise a push-pull capacitor C4 interconnecting the respective second input 14b and the respective second output 14c. The first input 16a of a first multiplier stage 12a and the first output 16e of a last multiplier stage 12d provide outputs for a load 42. The second input 14a of the first multiplier stage 12a provides an input for an AC voltage source. The buffer capacitor C3 of the first multiplier stage 12a comprises two series connected buffer capacitor parts C3a, C3b. An input 20 for the AC voltage source 34 is provided between the two buffer capacitor parts C3a, C3b.

14 Claims, 2 Drawing Sheets

(56) References Cited

U.S. PATENT DOCUMENTS

| | | | |
|---|---|---|---|
| 5,335,161 A * | 8/1994 | Pellegrino et al. | 363/61 |
| 2006/0210020 A1 | 9/2006 | Takahashi et al. | |
| 2008/0266914 A1 * | 10/2008 | Fischer | 363/61 |
| 2010/0135052 A1 * | 6/2010 | Luerkens | 363/61 |
| 2011/0075445 A1 * | 3/2011 | Drummond et al. | 363/15 |

* cited by examiner

VOLTAGE MULTIPLIER

CROSS-REFERENCE TO PRIOR APPLICATIONS

This application is the U.S. National Phase application under 35 U.S.C. §371 of International Application Serial No. PCT/IB2013/054497, filed on May 31, 2013, which claims the benefit of U.S. Application Ser. No. 61/661,858, filed on Jun. 20, 2012. These applications are hereby incorporated by reference herein.

FIELD OF THE INVENTION

The invention relates to a voltage multiplier, a high voltage power source and an X-ray imaging device.

BACKGROUND OF THE INVENTION

Voltage multipliers or cascade rectifiers are circuits which comprise diodes and so-called push-pull capacitors that are charged by an AC current via the diodes. The diodes and capacitors are arranged in multiplier stages in such a way that the voltage from a positive peak of the AC current is added to the voltage of a negative peak in each stage and the output voltage is doubled in each stage.

High voltage rectifiers for medical x-ray imaging devices frequently comprise a high voltage multiplier which multiplies the output voltage of a high voltage high frequency transformer to reach a required high output voltage of, for example, up to 160 kV. A disadvantage of those circuits may be that the root-mean-square-value of the pulse-like shaped current in the diodes is substantially higher than the average current, which is responsible for the output power and thus the losses in the diodes are significantly increased.

Another disadvantage of these circuits may be that the total current in the push-pull capacitor increase towards the transformer which may generate a high stress in the transformer-side push-pull capacitors. This may prevent the usage of small size ceramic capacitors for the push-pull capacitors.

In WO 2007/017793 A1 a proposal was made how to mitigate the pulse-shaped current in the diodes by adding additional equalizing capacitors. The additional equalizing capacitors are not subject to a DC bias and thus may be very small and cheap. With the design of WO 2007/017793 A1 the push-pull capacitor must be charged via the diodes of the last stage and the center tap of the transformer since all other DC current paths are now blocked by capacitors.

Another proposal avoids push-pull capacitors of the first stage by not grounding the transformer and leaving it in floating operation at an average of half of the voltage of the first multiplier stage. This allows a removal of the first two push-pull capacitors and thus removal of some relevant part of the losses.

SUMMARY OF THE INVENTION

It may be an object of the invention to provide a voltage multiplier with low losses.

This object is achieved by the subject-matter of the independent claims. Further exemplary embodiments are evident from the dependent claims and the following description.

An aspect of the invention relates to a voltage multiplier comprising a series of multiplier stages.

According to an embodiment of the invention, each multiplier stage comprises a first input, a second input, a first output and second output. The first and second outputs of a preceding multiplier stage are interconnected with first and second inputs of a subsequent multiplier stage. Each multiplier stage comprises two series connected diode elements having the same current conducting direction. The two series connected diode elements interconnect the first input and the first output and the second output is coupled between the two series connected diode elements. Each multiplier stage comprises a buffer capacitor interconnecting the respective first input and the respective first output. At least some multiplier stages comprise a push-pull capacitor interconnecting the respective second input and the respective second output. The first input of a first multiplier stage and the first output of a last multiplier stage provide outputs for a load. The second input of the first multiplier stage provides an input for an AC voltage source. The buffer capacitor of the first multiplier stage comprises two series connected buffer capacitor parts. Another input for the AC voltage source is provided between the two buffer capacitor parts.

It may be seen as a basic idea of the invention to eliminate the push-pull capacitors between the transformer and the first multiplier stage by realizing the buffer capacitor of the first stage as a tapped capacitor which tapping point is connected to the center tap of the secondary transformer winding. In this way, losses of these capacitors are avoided, and the first multiplier stage and further multiplier stages may be provided with equalizing capacitors, thus avoiding losses in the diodes.

Further aspects of the invention relate to a high voltage power source and an X-ray imaging device with such a voltage multiplier. These and other aspects of the invention will be apparent from and elucidated with reference to the embodiments described hereinafter.

BRIEF DESCRIPTION OF THE DRAWINGS

Below, embodiments of the present invention are described in more detail with reference to the attached drawings.

DETAILED DESCRIPTION OF EMBODIMENTS

Figure 1:
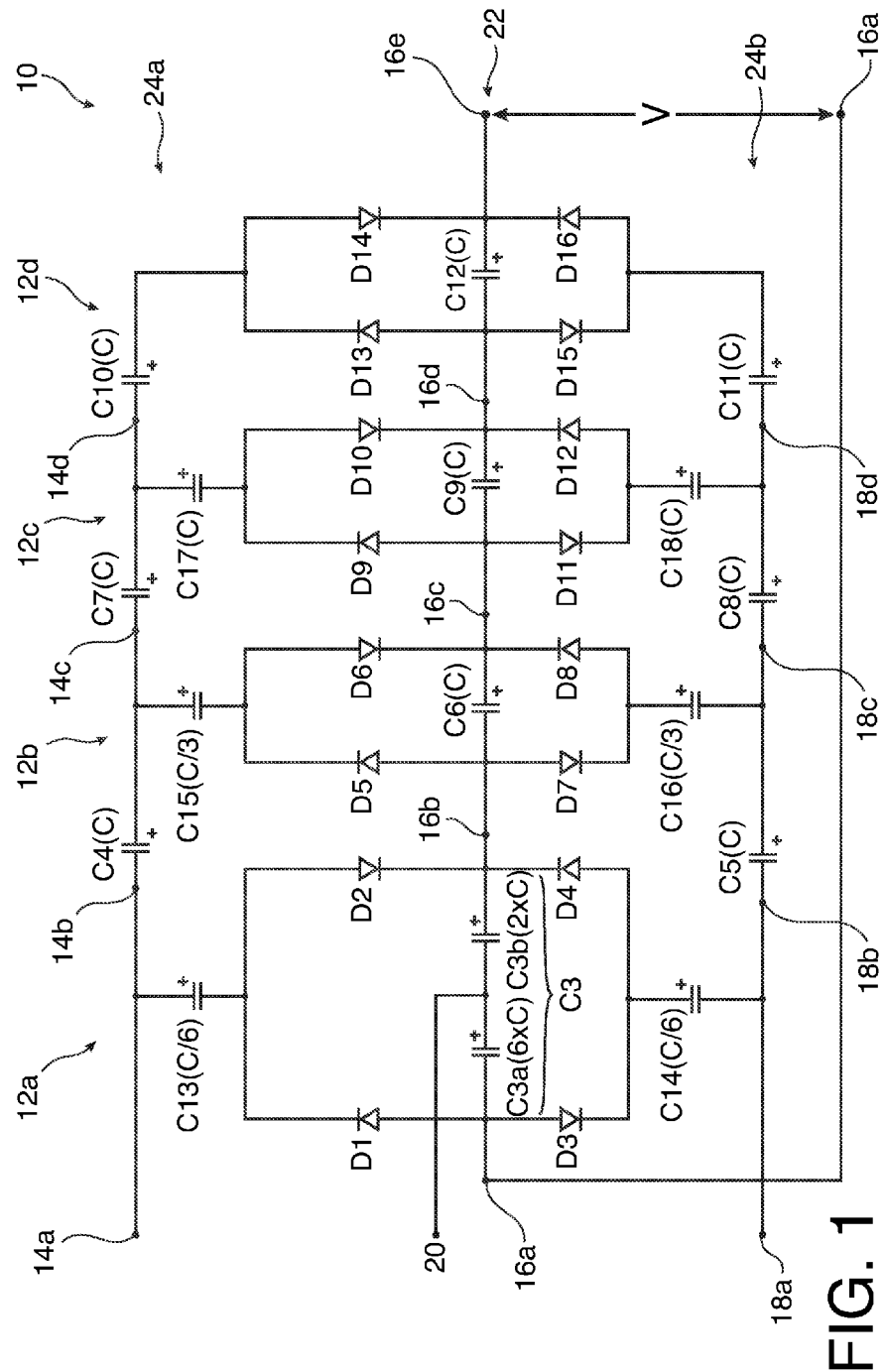
FIG. 1 shows a circuit diagram of a voltage multiplier according to an embodiment of the invention.

Fig. shows a voltage multiplier 10 comprising four multiplier stages 12a, 12b, 12c, 12d.

The first multiplier stage 12a comprises a first pair of diode elements D1, D2 connected in series and having the same conducting direction. Diode elements D1, D2 may each comprise one diode or a multitude of individual diodes connected in series.

A buffer capacitor C3 of the first multiplier stage 12a is connected between a first input of the multiplier stage 16a and a first output 16b. One end of the pair of series connected diode elements D1, D2 is connected to a first input 16a of the first multiplier stage 12a. The other end of the pair of series connected diode elements D1, D2 is connected to a first output 16b of the first multiplier stage 12a.

The pair of series connected diode elements D1, D2 is arranged such that a positive current may flow from the first input 16a to the first output 16b. This polarity has been chosen for easier understanding. The voltage multiplier 10 works likewise with negative polarity, as it may be chosen in an x-ray system. In the following the description is continued based on a positive output polarity.

One end of an equalizing capacitor C13 is coupled between the two diode elements D1, D2. The other end of the equalizing capacitor C13 is connected to a second input 14a of the first multiplier stage 12a and to a second output 14b of the first multiplier stage 12a, which are directly connected with each other.

The first multiplier stage 12a may comprise a second pair of series connected diode elements D3, D4 and a second equalizing capacitor C14 that are symmetrically arranged to the diode elements D3, D4 and the equalizing capacitor C13. The voltage multiplier 10 shown in FIG. 1 may be seen as a bipolar voltage multiplier 10, since, for each stage, it comprises two pairs of diode elements D1, D2, D3, D4. However, it is also possible that the voltage multiplier is a unipolar voltage multiplier with only one pair of diode elements D1, D2.

One end of the second pair of diodes D3, D4 is connected to the first input 16a. The other end of the second pair of diode elements D3, D4 is connected to the first output 16b. Like the pair of diode elements D1, D2, the pair of diode elements D3, D4 is arranged such that a positive current may flow from the first input 16a to the first output 16b.

Furthermore, one end of the equalizing capacitor C14 is coupled between the two diode elements D3, D4. The other end of the equalizing capacitor C14 is connected to a third input 18a of the first multiplier stage 12a and to a third output 18b of the first multiplier stage 12a, which are directly interconnected with each other.

Also the second, intermediate multiplier stage 12b (or the third, intermediate multiplier stage 12c) has these components, in particular, a first pair of diode elements, D5, D6 (D9, D10), and possibly a second pair of diode elements D7, D8 (D11, D12), a buffer capacitor C6 (C9) and an equalizing capacitors C15 (C17), and possibly C16 (C18).

The outputs 14b, 16b, 18b of the first multiplier stage 12a are the inputs 14b, 16b, 18b of the second multiplier stage, which has outputs 14c, 16c, 18c that are the inputs 14c, 16c, 18c of the third multiplier stage 12c. Analogously, the outputs 14d, 16d, 18d are the inputs 14d, 16c, 18c of the forth, last multiplier stage 12d.

The second multiplier stage 12b differs from the first multiplier stage 12a in that a first push-pull capacitor C4 is connected between the input 14b and one end of the equalizing capacitor C15. In such a way, the input 14b and the output 14c are decoupled by the capacitor C4. The second multiplier stage 12b also has a second push-pull capacitor C5 that is connected to one end of the equalizing capacitor C6 and that decouples the input 18b from the output 18c.

The third multiplier stage 12c is equally designed like the second multiplier stage 12b and also has two push-pull capacitors C7, C8.

The last multiplier stage 12d is similar to the intermediate multiplier stages 12b, 12d and has a pair of series connected diode elements D13, D14, and possibly a second pair D15, D16 that are interconnected by a buffer capacitor C12. However, the last multiplier stage 12d does not have equalizing capacitors but only push-pull capacitors C10, and possibly C11.

The output 16e of the last multiplier stage 12d and the input 16a of the first multiplier stage 12a provide the outputs 16a, 16e of the voltage multiplier 10. A load, for example an X-ray tube may be connected to these outputs 16a, 16e, which may provide a voltage of up to approximately 160 kV.

Since all but the first multiplier stage 12a comprises a (single) buffer capacitor C6, C9, C12 and two (single) push-pull capacitors C4, C5, C7, C8, C10, C11 and the multiplier stages 12b, 12c, 12d may be seen as series connected, the voltage multiplier comprise three chains of capacitors, a chain 22 of buffer capacitors C6, C9, C12, a first chain 24a of push-pull capacitors C4, C7, C10 and a second chain 24b of push-pull capacitors C5, C8, C11.

The inputs 14a, 18a of the first multiplier stage 12a provide a second input 14a and a second input 18a of the multiplier stage 10. A first input 20 is provided by tapping the buffer capacitor C3.

In particular, the first multiplier stage 12a differs further from the other multiplier stages 12b, 12c, 12d in that the buffer capacitor C3 comprises two capacitor parts C3a and C3b that may be series connected capacitors C3a, C3b. The buffer capacitor C3 also may be seen as a tapped capacitor C3. The tapping point 20 or the point 20 between the two capacitors C3a, C3b provides the first input 20 of the voltage multiplier 10.

The inputs 20, 14a, 18a may be connected to an AC voltage source, which provides an alternating voltage for the inputs 14a, 18a and a neutral point voltage for the input 20. With the alternating voltage at the inputs 14a, 18a, the cascade of multiplier stages 12a to 12d charges the capacitors C3 to 12 with raising voltage values to generate a DC output voltage at the outputs 16a, 16e.

The voltage multiplier 10 may be used in high voltage rectifier modules for x-ray imaging devices (for example medical, material analysis and/or baggage inspection imaging devices) and other high voltage generators, for example in electrostatic particle filters.

Figure 2:
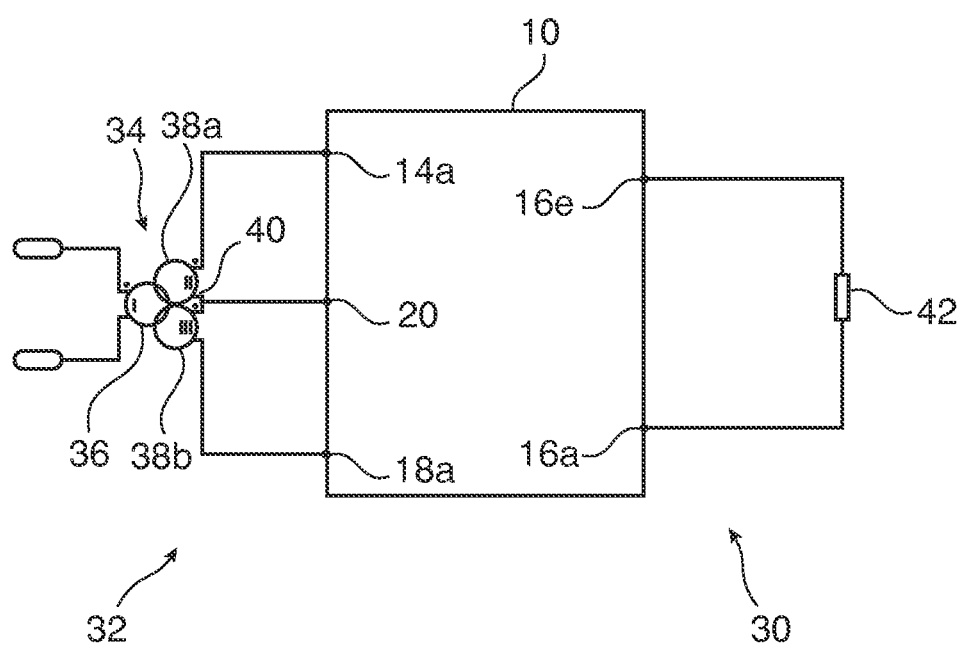
FIG. 2 schematically shows high voltage components of an X-ray imaging device according to an embodiment of the invention.

For example, FIG. 2 shows an X-ray imaging device 30 comprising a high voltage source 32 with the voltage multiplier 10. The inputs 14a, 20, 18a are connected to a transformer 34 of the high voltage source 32 with one primary winding 36 and two secondary windings 38a, 38b connected in series. The neutral point input 20 of the voltage multiplier 10 is connected between the secondary windings 38a, 38b to a center tap 40 of the transformer 32. Thus, the transformer center tap 40 is connected to the tap 20 between the two capacitors C3a, C3b. The other two inputs 14a, 18a are connected to the other ends of the secondary windings 38a, 38b. The primary winding of the transformer 34 may be supplied with a voltage from a power grid.

By dividing the buffer capacitor C3 into two separate capacitors (C3a and C3b), the voltage multiplier 10 may use equalizing, current shaping capacitors C13 to C18 without the need for push-pull capacitors in the first multiplier stage 12a, i.e. push-pull capacitors that are interconnecting the inputs 14a, 18a with the equalizing capacitors C13, C14.

With the avoidance of the push-pull capacitors of the first multiplier stage 12a, also the losses with respect to these capacitors may be avoided. With the equalizing capacitors C13 to 18, which may be small AC-capacitors C13 to C18, furthermore losses in the diode elements may be reduced. As depicted in WO 2007/017793 A1 the capacitors C13 to C18 are only exposed to an AC-load and do not subject to a DC bias, as appropriate charging of the complete push-pull chain is achieved. This may allow the usage of very small capacitors C13 to C18 which do not contribute relevantly to size and cost of the system.

However, bias-conditions on the capacitors C13 to C18 may occur again, if the center tap 40 of the transformer 34 is not connected to the ground input 20, in order to remove the above mentioned push-pull capacitors of the first multiplier stage 12a. The basic reason for this effect is the inability to establish the bias charge along the push-pull capacitors chain, because all DC current paths in this chain are blocked by capacitors.

All push-pull capacitors C4, C5, C7, C8, C10, C11 may have the same capacitor value, for example the value C. Also all buffer capacitors C6, C9, C12 may have the same capacity value, which may be equal to the capacity value C of the push-pull capacitors.

The equalizing capacitors C13, C14 of the first multiplier stage 12a may have a capacity value of C/6. The equalizing capacitors C15, C16 of the second multiplier stage 12b may have a capacity value of C/3. The equalizing capacitors C17, C18 of the third multiplier stage 12c may have a capacity value of C.

The capacitor C3a which is connected to the ground 20 may have a value of 6C, while the capacitor C3b may have a value of 2C. This dimensioning of the capacitors leads in combination with the bias charge of the remaining push-pull capacitors C4, C5, C7, C8, C10, C11 to an equal voltage of over the two capacitors C3a and C3b and also to the correct voltage at all capacitors of the push-pull chains, thus avoiding bias voltage over the equalizing capacitors.

During start-up of the voltage multiplier 10, all DC-biased capacitors C4 to C12, i.e. the buffer capacitors and the push-pull capacitors, are charged to a nominal fraction (e.g. ¼) of the output voltage V between the outputs 16e, 16a, which requires a DC current flow for some time in the capacitors C4 to C12. After the end of this phase, all capacitors C4 to C12 should have a voltage of a fraction of the output voltage V. Namely, the tapped capacitor C3 should have half of this voltage at each of the two parts C3a and C3b. It may be also assumed, that the equalizing, current-shaping capacitors C13 to C18 do not have a DC bias after completion of the start-up.

The charging current of the push-pull chains 24a, 24b is now going from the last rectifier stage 12d through each chain 24a, 24b of push-pull capacitors and through the transformer 34 and the capacitor C3a to the ground 20. This would result in an additional increase of the voltage at the capacitor C3a if the capacitor C3a is not increased compared to the other capacitors. The capacitor C3a usually must store the sum of the charges of the buffer chain 22 and the two push-pull chains 24a, 24b at half of the voltage of the first multiplier stage 12a.

In general, the capacity value of the first buffer capacitor part C3a is proportional to the sum of the capacity values of the series connections 24a, 24b of the push-pull capacitors C4, C5, C7, C8, C10, C11 and the capacity value of the series connection of the buffer capacitors C6, C9, C12 of all but the first stage.

In the case of a bipolar voltage multiplier 10 as Shown in FIG. 1 and in the case all capacitors have the same capacity value C, these values are C/(n−1) for the chains, 24a, 24b and 22 resulting in a sum of 3C/(n−1), where n is the number of stages.

In the case of a unipolar voltage multiplier, there are only the chains 24a and 22 and the sum is 2C/(n−1).

Since it is assumed, that the first multiplier stage 12a is at half of the voltage and has to store the sum of the charges, the above sum is multiplied by 2(n−1), resulting in a value of 6C for a bipolar voltage multiplier or 4C for a unipolar voltage multiplier.

The capacity value of the second buffer capacitor part C3b is proportional to the capacity value of the series connection of the buffer capacitors C6, C9, C12 of all but the first stage. In the case all capacitors have the same capacity value C, this value is C/(n−1) for the chain 22. Analogously to the capacitor C3a, for C3b this results in 2C for the capacitor C3b.

For voltage capability reasons, the buffer capacitors C3, C6, C9, C12 in a voltage multiplier 10 may be formed of several capacitors in series, so a center tap of the capacitor C3 may exists already in all cases when an even number of capacitors in series is used to realize C3. While the part C3b remains unchanged, the part C3a may have to be tripled in capacity.

Practically this resembles shifting the former push-pull capacitors from their AC position into a parallel connection to half of the lowermost buffer capacitor. However, the ripple current load in the DC buffer chain 22 is by far much less than in the push-pull chains 24a, 24b so that the losses in AC-capacitors C13 to C18 may be almost entirely eliminated. Instead of bulky and expensive AC-capacitors C13 to C18 much smaller (e.g. ceramic) or cheaper DC-type capacitors C13 to C18 may be used.

Summarized, an arrangement of push-pull capacitors C4, C5, C7, C8, C10, C11 and buffer capacitors C6, C9, C12 is disclosed which eliminates a number of push-pull capacitors while maintaining low-stress waveforms in the rectifier diode elements D1 to D16. The costs of the high voltage rectifier may be reduced, efficiency may be improved and smaller size may be realized, which may be especially relevant for medical x-ray imaging, in particular for CT and CV applications.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. A single processor or controller or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A voltage multiplier comprising a series of multiplier stages,
   wherein each multiplier stage comprises a first input, a second input, a first output and second output, the first and second outputs of a preceding multiplier stage interconnected with first and second inputs of a subsequent multiplier stage;
   wherein each multiplier stage comprises two series connected diode elements having the same current conducting direction, the two series connected diode elements interconnecting the first input and the first output and the second output being coupled between the two series connected diode elements;
   wherein each multiplier stage comprises a buffer capacitor interconnecting the respective first input and the respective first output;
   wherein at least some multiplier stages comprise a push-pull capacitor interconnecting the respective second input and the respective second output;
   wherein the first input of a first multiplier stage and the first output of a last multiplier stage provide outputs for a load;
   wherein the second input of the first multiplier stage provides an input for an AC voltage source;
   wherein the buffer capacitor of the first multiplier stage comprises two series connected buffer capacitor parts;
   wherein an input for the AC voltage source is provided between the two buffer capacitor parts.

2. The voltage multiplier of claim 1,
wherein all multiplier stages but the first multiplier stage comprise a push-pull capacitor interconnecting the respective first input and the respective first output.

3. The voltage multiplier of claim 1,
wherein at least some multiplier stages comprise an equalizing capacitor with one end connected to the respective second output and the other end connected between the two series connected diode elements.

4. The voltage multiplier of claim 1,
wherein all multiplier stages but the last multiplier stage comprise an equalizing capacitor with one end connected to the respective output and the other end connected between the two series connected diode elements.

5. The voltage multiplier of claim 1,
wherein the buffer capacitor of the first multiplier stage comprises a tapped buffer capacitor, the tapped buffer capacitor providing two buffer capacitor parts and having a tapping point between a first capacitor part and the second capacitor part.

6. The voltage multiplier of claim 1,
wherein each multiplier stage comprises a second pair of series connected diode elements having the same current conducting direction, the second pair of series connected diode elements interconnecting the first input and the first output and a third output being coupled between the second pair of series connected diode elements;
wherein at least some multiplier stages comprise a second push-pull capacitor interconnecting a respective third input and a respective third output.

7. The voltage multiplier of claim 6,
wherein at least some multiplier stages comprise a second equalizing capacitor with one end connected to the respective third output and the other end connected between the second pair of series connected diode elements.

8. The voltage multiplier of claim 1,
wherein the buffer capacitors of all but the first multiplier stage have the same capacitor value.

9. The voltage multiplier of claim 1,
wherein the push-pull capacitors of all but the first multiplier stage have the same capacitor value.

10. The voltage multiplier of claim 1,
wherein all multiplier stages but the last multiplier stage comprise an equalizing capacitor and the capacity value of the equalizing capacitors is increasing from multiplier stage to multiplier stage.

11. The voltage multiplier of claim 1,
wherein the capacity value of a first buffer capacitor part of the first multiplier stage which is connecting the first input of the first multiplier stage with the input for the AC voltage source, is proportional to the sum of the capacity value of the series connection of the push-pull capacitors and the capacity value of the series connection of the buffer capacitors of all but the first stage.

12. The voltage multiplier of claim 1,
wherein the capacity value of a second buffer capacitor part of the first multiplier stage which is connecting the first output of the first multiplier stage with the input for the AC voltage source, is proportional to the capacity value of the series connection of the buffer capacitors of all but the first stage.

13. A high voltage power source, comprising:
a voltage multiplier according to claim 1,
a transformer as AC voltage source,
wherein a tapping point of the transformer is connected to the input for the AC voltage source.

14. An X-ray imaging device, comprising:
a voltage multiplier according to claim 1,
an X-ray tube as load.

* * * * *